United States Patent [19]

Patatano

[11] Patent Number: 5,501,808
[45] Date of Patent: Mar. 26, 1996

[54] CRYSTALLINE-LIKE TRANSITION METAL MATERIAL

[76] Inventor: Philip Patalano, 521 Lauiki St. #6, Honolulu, Hi. 96826

[21] Appl. No.: 228,782

[22] Filed: Apr. 18, 1994

[51] Int. Cl.$^6$ .......................... C01G 49/00; C01G 53/00; C01G 55/00
[52] U.S. Cl. ...................... 556/28; 423/414; 556/112; 556/46; 556/58; 556/136; 556/140
[58] Field of Search .................... 423/414, 439, 423/440, 441; 252/62.51; 556/46, 58, 140, 112

[56] References Cited

U.S. PATENT DOCUMENTS

| | | | |
|---|---|---|---|
| 1,544,197 | 6/1925 | Terry | 423/414 |
| 2,113,355 | 4/1938 | McKenna | 423/414 |
| 2,729,689 | 1/1956 | Blanchard et al. | 556/12 |
| 4,683,315 | 7/1987 | Lippard et al. | 556/12 |
| 4,789,534 | 12/1988 | Laine | 423/241 |
| 5,102,646 | 4/1992 | Bienvenu | 423/439 |

OTHER PUBLICATIONS

Barral et al., Inorg. Chimica Acta, 31 (1978) 165–169 no month.
Masai et al., J. Org. Met. Chem., 26, 271–276 (1971) no month.
Talt et al., J. Am. Chem. Soc. (1989) 111, Abstract no month.
Khan et al., J. Org. Met. Chem., 424 (1992) 82–97 no month.
S. Brown, British Association Reports, pp. 37–40 (1839) Aug.
Schutzenberger et al., Bull. Soc. Chim. (2) 35, 355 (1881) Feb.
W. Wittorf, Z. Anorg. Chem. 89, 1–74 (1914) no month.
J. F. Durand, Compt. Rend. 177, 193–195 (1923) Oct.
Von R. Nast et al., Z. Anorg. Allg. Chem. 279, 146–156 (1955) no month.
R. Nast et al., Alkinylverbindungen von Übergangsmetallen (XVI), 96, 1478–1483 (1962) no month.
R. Nast et al., Alkinylverbindungen von Übergangsmetallen (XVI), 96, 1470–1477 (1962) no month.
T. Nast, Angew. Chem. 72, 26–31 (1960) no month.
Sonogashira et al., J. Organomet. Chem., 188, 237–243 (1980) no month.
Takahashi et al., The Inst. of Scien. & Ind. Res., pp. 247–251 no date.
F. von Kügelgen, Z. Elektrochem 7, 541, 547, 573 (1901) Apr.
B. Nuemann, Chem. Zig. 24, 1013 (1901) no month.
Von A. Schneider, Z. Allorg. Allg. Chem. 279 (1955) no month.
T. K. Menshichikova, Vyzokochist. Veshchestva N6:36–41 (1991) no month.
Kügelgen, Von Fr. v., Chemiker—Zeitung No. 97, p. 1060 Nov. 1900.

Primary Examiner—C. Melissa Bonner
Attorney, Agent, or Firm—Millen, White, Zelano & Branigan

[57] ABSTRACT

Transition metal compounds of a crystalline-like structure are provided having unique electrical properties. The compounds comprising nickel have been shown to have ferromagnetic behavior which is induced or enhanced by exposure to electromagnetic radiation and heat. The compounds are identified by characteristic peaks in the infrared spectra and X-ray powder diffraction spectra. The spectra suggest the compounds have a planar structure of the empirical formula $M(X)_{(4-Y)/X}M_C(Y)C_4$ or a three-dimensional structure of empirical formula $M(X)_{(6-Y)/X}M_C(Y)C_6$, wherein $M_C(Y)$ is the transition metal, with Y being its ionic state, and M(X) is the counter cation with X being its ionic state.

42 Claims, 5 Drawing Sheets

CRYSTALLINE-LIKE TRANSITION METAL MATERIAL

FIELD OF THE INVENTION

This invention relates to materials having a crystalline-like structure which comprise transition metals that exhibit unique electronic properties.

BACKGROUND OF THE INVENTION

The development of new materials with intrinsic parameters which affect electronic properties has become increasingly more important and has begun to encompass a variety of scientific disciplines. Covalent crystalline materials containing delocalized pi systems are known to exhibit interesting electronic properties when combined with other characteristics such as partially filled electronic energy levels and certain types of electron-phonon coupling. See, for example, C. Kittel, *Introduction to Solid State Physics*, 6th Ed., John Wiley & Sons, Inc., New York (1986), pp. 338–340. Examples of materials that have these properties are intercalated graphite and n-doped polyacetylenes described by Zhu et al., *Nature*, Vol. 355, pp. 712–714 (1992), p-doped polyaniline described by MacDiarmid et al., *Synth. Met.*, 18, p. 285 (1987), sulfur nitride (SN) described by Labes et al., *Chem. Rev.*, 79, p. 1 (1979), and intercalated $C_{60}$ described by Haddon et al., *Nature*, Vol. 350, pp. 320–322 (1991). These materials can exhibit a range of parameters from semiconductor to metallic-like conductivities and many are superconducting. For example, the intercalated $C_{60}$ material can have a superconducting conversion temperature ($T_C$) as high as 45 K.

Some copper oxide containing compounds have been found to have a $T_C$ value as high as 125 K, which is believed to be due to planes of copper and oxygen that extend through these materials. See, R. J. Cava, *Sci. Amer.*, 263 (2), pp. 42–49 (1990). Copper and oxygen atoms positioned within a plane form only 90° and 180° angles for bonding. Such bonding may have an important impact on the electronic system since the d and p electron orbitals for the atoms are orthogonal to each other. The performance of the copper oxide containing compounds has raised interest in investigating materials with a structure and dimensionality similar to a copper-oxygen plane. Materials which geometrically mimic a planar structure are Hofmann clathrates and the best known of these is $Ni(CN)_2 \cdot NH_3 \cdot C_6H_6$ disclosed by Iwamoto, *Inclusion Compounds*, Vol. 1, pp. 29–42, Academic Press, London (1984). However, the material's electronic properties are not very interesting. It is a very good insulator and has the predicted negative resistance versus temperature slope for insulators. There is no evidence of pi delocalization over the crystal structure. It is believed the delocalized pi system in these compounds is limited and extends only over the units of $[Ni(CN)_4]^{2-}$. Other compounds with structures which mimic a Cu-O plane are "Prussian Blues" described by Shriver et al., *Inorg. Chem.*, 4(5), pp. 725–730 (1965). These compounds differ in the respect that the networks are three-dimensional, consisting of octahedral transition metals interlinked by linear cyanide units. These compounds are not clathrates and contain counter ions such as alkali metals in the lattice. Delocalization in these compounds is also limited and is believed to extend only over the units of $[M(X)(CN)_6]^{-6+x}$, wherein X is the oxidation state of the transition metal and is in general +2 or +3. It is desirable to provide compounds wherein the pi delocalization is extended further than that of the copper oxide-planes to obtain novel electronic properties.

SUMMARY OF THE INVENTION

It is an object of the present invention to provide a compound wherein the quantity and geometry (dimensionality) of the delocalized pi systems are distinguished from those of copper oxide compounds to obtain novel electronic properties.

It is another object of the present invention to provide a compound with a structure analogous to a copper oxide plane with bonding angles of 90° and 180°.

It is another object of the present invention to provide a transition metal material with a unique crystalline-like structure.

It is a further object of the present invention to provide a unique ferromagnetic compound comprising nickel, iron or cobalt having unique ferromagnetic properties.

It is another object of the present invention to provide a method for preparing the transition metal materials and ferromagnetic compounds of the present invention.

It is another object of the present invention to provide a crystalline-like compound comprising transition metal and acetylide linkages ($C_2^{2-}$).

To accomplish these objectives, there is provided by the present invention planar compounds comprising transition metals selected from the group consisting of Ni(II), Pd(II), Pt(II), Au(III), Ir(I), Rh(I), and three dimensional compounds comprising transition metals selected from the group consisting of Fe(II), Fe(III), Co(II), Co(III), Cr(III), Mn(II), Mn(III), Mo(II), Os(II), Rh(III), Ru(III) and Ir(III), wherein the infrared spectra of these compounds have a fingerprint peak within the range of 595–655 cm$^{-1}$ for the metal-carbon stretch. In preferred embodiments, the compounds are ferromagnetic, comprise nickel, iron or cobalt, have a density below 5 g/cm$^3$ and show enhanced ferromagnetism when exposed to light or thermal energy. Planar compounds such as those comprised of nickel have a density below 5 gm/cm$^3$. Three dimensional compounds such as those comprising Fe or Co have a density below 3 gm/cm$^3$.

Methods for producing these novel compounds are also provided which include reacting calcium carbide ($CaC_2$) with nickel chloride ($NiCl_2$) or related compounds at a temperature above 300° C. in an inert atmosphere.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

The transition metals useful in forming the crystalline-like compounds having a planar structure are those capable of forming square planar complexes such as Ni(II), Pd(II), Pt(II), Au(III), Ir(I) and Rh(I). Such transition metal species provide bonding angles of 90° and 180°. The transition metals contemplated for use in crystalline-like compounds having 3-D networks are capable of forming octahedral complexes with carbon. These include Fe(II), Fe(III), Co(II), Co(III), Cr(III), Mn(II), Mn(III), Mo(II), Os(II), Rh(III), Ru(III) and Ir(III). These transition metals provide the appropriate bonding angle consistent with copper oxide planes. In forming the transition metal planes or three-dimensional network, the transition metal is reacted with a coordinating compound or ligand to complete the crystalline structure of the compound.

The invention includes compounds with only one transition metal as well as those with mixtures of transition metals having the same coordination characteristics which form either planar or 3-D structures. The molar ratio of the transition metals within the compound can vary widely. A continuous ratio of mixing is possible. Mixed transition metals have been shown in the planar Hofmann clathrates described by Iwamoto, supra; the "Prussian Blues" described by Shriver et al., *supra*, and the poly(yne) compounds described by Sonogashira et al., *J. Organomet. Chem.* 160, pp. 319–327 (1978). The compounds of the present invention comprise transition metals as described above in a coordinated crystal structure such that a metal-carbon stretch provides a broad fingerprint peak within the range of 595 to 655 cm$^{-1}$ within its infrared spectra. The hydrated form of the crystalline-like compounds of this invention which comprise nickel have a fingerprint peak of about 625 cm$^{-1}$ in the IR spectra and a fingerprint peak of about 7.98 Å in the X-ray powder diffraction spectra.

The unit cells for these crystalline-like compounds can be planar or 3-dimensional, depending on the transition metal used. The size of the unit cell also varies with the transition metal(s) utilized. Two axes (a and b) for the unit cell of the planar crystalline structure have a dimension which is a multiple of a value in the range of 4.90 Å to 5.10 Å. The value multiplied depends on the transition metal due to the varying size of the bond lengths. The multiplier, N, is typically from 1–1000, more typically less than 100. Therefore, the range of dimensions for the axes a and b can be represented as 4.9 ÅN to 5.1 ÅN. The axes a and b do not have to have equivalent dimensions. The distance between the planes can vary from 3.5 Å to 4.5 Å for non-hydrated compounds and 3.5–10Å for intercalated or hydrated compounds. The C axis is some multiple of the distance between planes. For nickel compounds, the dimensions of the two axes a and b are both about 10.13 Å (N=2) and the distance between planes is believed to be about 6.75 Å with a C-axis of about 13.25 Å.

The unit cell for three dimensional compounds have axes a, b and c with dimensions represented by multiples of a value in the range of 4.9 Å to 5.1 Å, depending on the transition metal. The multiplier, N, is also typically from 1–1000, more typically less than 100. Therefore, the range of dimensions for the axes a, b and c can be represented as 4.9 Å N to 5.1 Å N. The axes a, b and c do not have to have equivalent dimensions.

Where more than one transition metal is used and the compound is crystalline, the dimensions of the unit cell is expected to fall within the ranges above. However, with mixed transition metals, the compound's structure may be completely random with respect to the order of transition metals with no definable unit cell.

Figure 1:
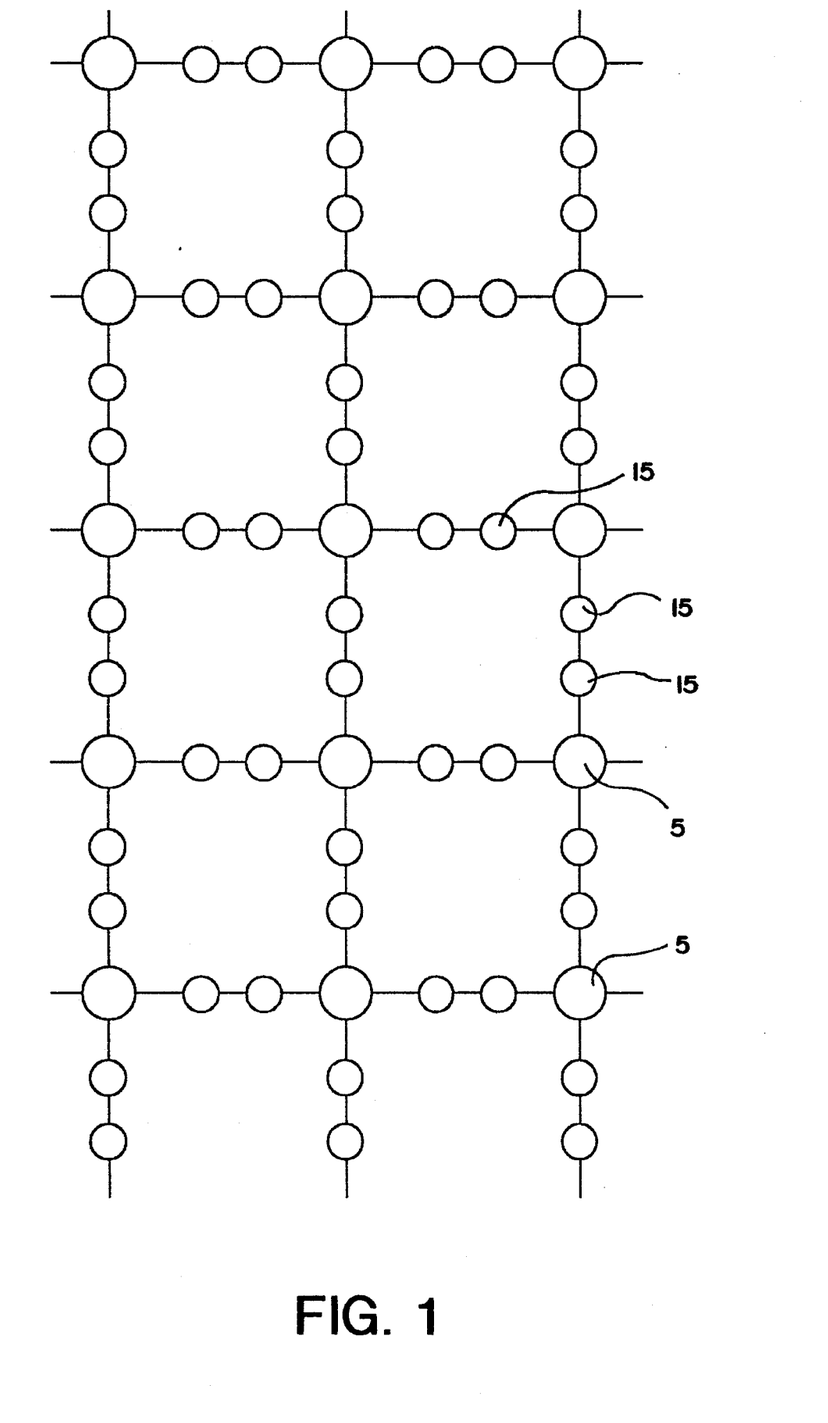
FIG. 1 is a representation of the partial atomic structure of a planar compound of the present invention.

Not wishing to be bound by theory, it is believed that the transition metal is coordinated with acetylide, $C_2^{2-}$, segments. This theory is consistent with the products expected from the starting materials utilized in forming the transition metal crystal structures; the size of the unit cell of crystalline-like nickel compounds, as extrapolated from X-ray powder diffraction data and the unique electronic properties of the compounds obtained. Pursuant to this theory, a partial unit cell (counter cations not shown) for a four coordinated transition metal bonded to acetylide has the structure shown below:

wherein $M_C(Y)$=a four coordinated transition metal. An example of a partial unit cell (counter cations not shown) for a six coordinated transition metal bonded to acetylide has the structure shown below:

Not wishing to be bound by theory, it is believed the planar crystalline transition metal compounds of the present invention are of a structure as shown in FIG. 1, where only transition metals 5 and acetylene carbons 15 are shown. The counter cations are not shown in FIG. 1 and are believed to extend between the planes. The empirical formula for compounds with a structure as shown in FIG. 1 is $M(X)_{(4-Y)/x}M_C(Y)C_4$, wherein $M_C(Y)$ is the transition metal, with Y being its ionic state and M(X) being the counter cation with X being its ionic state. M(X) is typically an alkali metal, alkaline earth metal or rare earth metal or stable cation such as an ammonium ion ($NH_4^+$). Such a structure will provide a delocalized pi system over a significant portion of the compound. Planar compounds of the formula $M(X)_{(4-Y)/x}M_C(Y)C_{4n}$ wherein n=1–6 will also provide a delocalized pi system. In such a compound, more than one acetylene group is bonded between the metal atoms.

Figure 2:
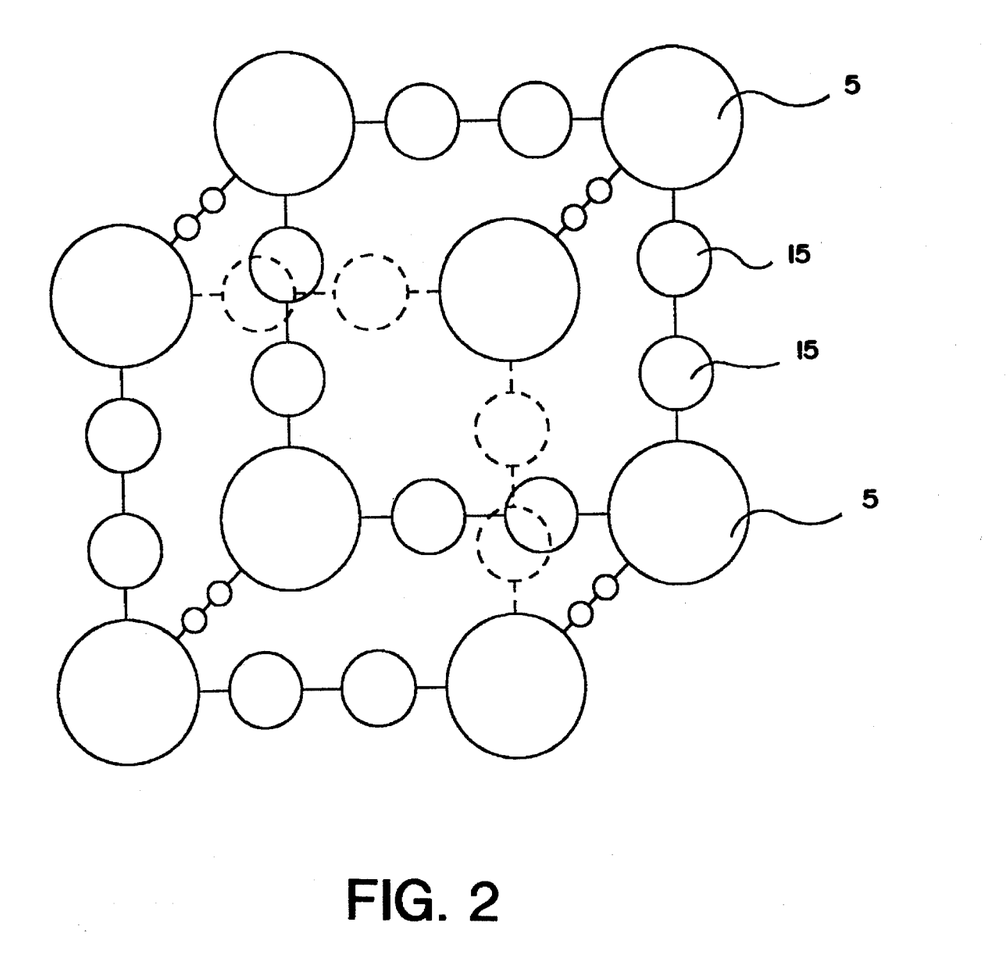
FIG. 2 is a representation of the partial atomic structure of a 3-D compound of the present invention.

In the crystalline compounds of the present invention having three dimensional crystal structure, the coordinating compounds or ligands extend between planes. Not wishing to be bound by theory, where the coordinating compound or ligand is an acetylide ($C_2^{2-}$), it is believed the 3-D crystalline network has a structure as shown in FIG. 2. The empirical formula for such a crystalline compound is $M(X)_{(6-Y)/x}M_C(Y)C_6$, wherein $M_C(Y)$ is a transition metal, with Y being its ionic state, and M(X) being the counter cation with X being its ionic state. Three dimensional compounds of the formula $M(X)_{(6-Y)/x}M_C(Y)C_{6n}$ wherein n=1–6, also provide a delocalized pi system.

Figure 3A:
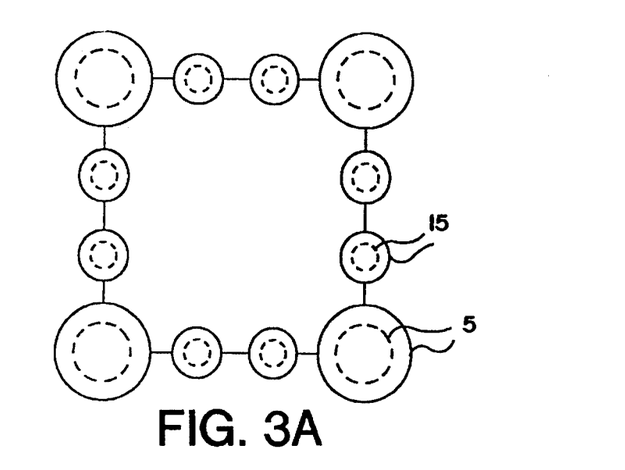
FIGS. 3A–C are representations of possible stacking arrangements for planar compounds of the present invention.
Figure 3B:
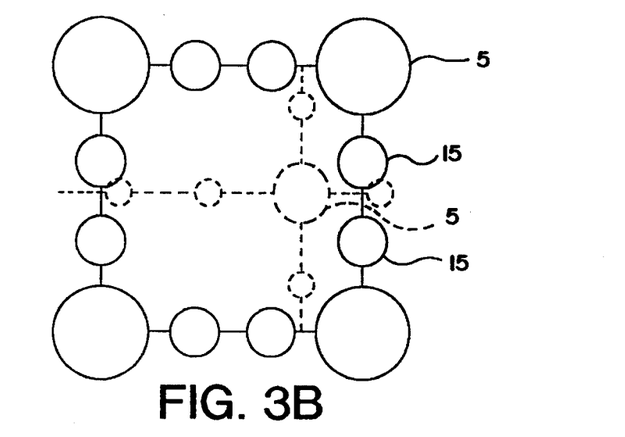
Figure 3C:
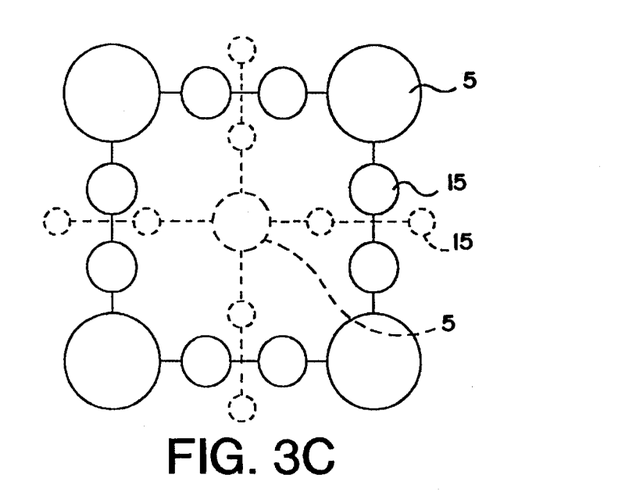

As shown in FIGS. 3A–3C, the planar structures can have many orientations including eclipsed, staggered or centered.

The eclipsed form, shown in FIG. 3A, makes the planes superimposed and is a tetragonal unit cell since $a=b\neq c$ and the bond angle $\alpha=\beta=\gamma 90°$. The c axis is given as the interplanar distance. This type of geometry has been seen in certain transition metal cyanides as disclosed by Miller et al., *Prog. Inorganic Chem.*, Vol. 20, pg. 1 (1975). The staggered form, shown in FIG. 3B, has many combinations and places the planes at some orientation other than eclipsed or centered. The sequence could be ABA where the A planes are in the same orientation and the B planes are staggered. A special case of staggered is centered, shown in FIG. 3C. In this case, the c axis is twice the interplanar distance.

When the counter cations are considered in the structures given in FIGS. 1 and 2, the unit cells will remain in the tetragonal crystal system if their arrangement is the same for each unit. When the counter cations have repeat patterns that encompass more than one unit, then the crystal system can change. When the pattern is only along the c axis, the tetragonal system is maintained. If it is along either the a or b axes, then the system can become orthorhombic wherein $a\neq b\neq c$; however, $\alpha=\beta=\gamma=90°$.

When considering the crystal structures for the 3-D networks as shown in FIG. 2, it is usually seen that the cell unit is cubic without consideration of the counter cations. ($a=b=c$ and $\alpha=\beta=\gamma=90°$). This would be true because the connectivity is the same along three crystallographic axes. When the counter cations are considered, the crystal system can become either tetragonal or orthorhombic, depending on the direction of the counter cation repeat pattern.

Dimeric and oligomeric forms of these proposed compounds have been synthesized by Takahashi et al. The Institute of Scientific and Industrial Research, pp 247–251. The compounds of the present invention are more delocalized and partially ionic in character and thus have stabilities greater than known non-ionic linear transition metal acetylide polymers. The compounds of the present invention, like the linear transition metal acetylides, can obtain high molecular weights. However, the compounds of this invention are two-dimensional and three-dimensional in structure with many compounds being ceramic-like.

Compounds of the present invention can be produced by reacting anhydrous transition metal halide with alkali metal and/or alkaline earth metal acetylides ($C_2^{2-}$=acetylide) in an inert atmosphere following mixing at a temperature of at least 300° C., preferably at the eutectic temperature of the transition metal halide and the alkali metal/alkaline earth metal halide for at least 3 minutes to more than one hour. For example, the eutectic temperature of $NiCl_2$ and $CaCl_2$ is about 600° C. Two or more transition metal halides can be reacted to provide compounds with mixed transition metals. A mixture of black and white powder is obtained from this reaction. The formation of a black powder is noticed as the reaction progresses until a color change is complete. This method was used to prepare the crystal-like compositions of this invention comprising nickel with the following stoichiometry $$NiCl_2(S)+2CaC_2(S)\rightarrow CaNiC_4(S)+CaCl_2(S).$$

A more general formula is as follows:

$$M_C(Y)Z_y + 2M(X)_{2/x}C_2 \rightarrow M(X)_{(4-y)/x}M_C(Y)C_4 + \frac{Y}{X}M(X)Z_x$$

where Z is a halogen.

This method is preferred and preferably, the reaction volume is minimized to minimize sublimation loss of $NiCl_2$. Purification of the product is accomplished by extracting calcium chloride and unreacted nickel chloride with an alcohol. Calcium carbide may also be removed by reaction with an alcohol. The planar structure and the presence of acetylide ligands are consistent with X-ray powder diffraction analysis.

Other methods are also suitable, such as reacting within a solvent a transition metal tetraacetylide complex of the formula $M(X)_{(4-y)/x}M_C(Y)(C_2H)_4$ and a transition metal salt of the formula $M(X)_{(4-y)/x}M_C(Y)Z_4$ in the presence of a catalyst such as a copper (I) salt of the formula $Cu(I)Z$, $AgClO_3$, AlBN or $Bu_3B/O_2$, wherein M(X) and $M_C(Y)$ are as defined above and Z is preferably a halide or carboxylate. Two or more transition metal halides and/or two or more transition metal tetraacetylide complexes can be reacted to provide compounds with mixed transition metals.

An additional method for preparing a metal compound having a 3-D crystalline structure comprises reacting within a solvent a transition metal hexaacetylide complex of the formula $M(X)_{(6-y)/x}M_C(Y)(C_2H)_6$ and a transition metal salt of the formula $M(X)_{(6-y)/x}M_C(Y)Z_6$ in the presence of a catalyst such as a copper (I) salt of the formula $Cu(I)Z$ (where Z is preferably halide or carboxylate) $AgClO_3$, AlBN or $Bu_3B/O_2$. In preferred embodiments, the transition metal is nickel. Two or more transition metal halides and/or two or more transition metal tetraacetylide complexes can be reacted to provide compounds with mixed transition metals.

The tetraacetylide complex can be obtained by a novel method of this invention wherein acetylene is reacted in a solvent with a transition metal salt of the formula $M(X)_{(4-y)/x}M_C(Y)Z_4$ in the presence of a catalyst such as a copper (I) salt, $Cu(I)Z(Z=halide)$ $AgClO_3$, AlBN or $BuB/O_2$ according to the following reaction $$M(X)_{(4-y)/x}M_C(Y)Z_4+4H_2C_2\rightarrow M(X)_{(4-y)/x}M_C(Y)(C_2H)_4+4HZ.$$

The hexaacetylide complex can be obtained by a similar reaction scheme with the same catalysts wherein equivalents of acetylene are reacted in a solvent with $M(X)_{(6-y)/x}M_c(Y)Z_6$ to provide $M(X)_{(6-y)/x}M_c(Y)(C_2H)_6$.

Alternatively, the tetraacetylide complex can be obtained by conventional means, such as reacting a transition metal thiocyanate or cyanide with an alkali earth metal salt of acetylide in solvent. The hexaacetylide complexes can be obtained by similar techniques wherein a corresponding transition metal thiocyanate is reacted with an alkali metal salt of acetylide.

These are only some examples of methods for chemically linking to transition metal atoms with acetylenic carbons. The most useful types are copper salt catalyzed reactions (Cu(I)Z) between transition metal complexes and acetylenes. This works well for Pt and Pd but not for Ni since the complexes form precipitates in amine solutions. The choice of Z is preferably limited to halides or possibly saturated carboxylates. The most stable catalyst is copper (I) iodide. These reactions should be carried out in the absence of $O_2$ since oxygen can cause oxidative coupling between the acetylides.

When transition metals having ferromagnetic properties are used in the crystalline-like compounds of the present invention, these crystal structures also exhibit ferromagnetic behavior. They are of low density, typically below 5 g/cm³ for planar compounds and below 3 g/cm³ for 3-D compounds, and also exhibit unusual electronic behavior.

Photoferromagnetic and thermoferromagnetic properties have been found to exist in compounds comprised of nickel. In addition, a nonlinear ferromagnetic response with respect to an externally applied magnetic field has been found.

The compounds containing nickel have been obtained by heating nickel chloride and calcium carbide in an inert atmosphere following mixing and heating under the conditions described in the examples. The nickel compound is hygroscopic and reacts with a large excess of water to produce a mixture of nickel hydroxide, calcium hydroxide and acetylene gas. The hygroscopic formula being $CaNiC_4 \cdot xH_2O$, wherein x is believed to be between 2 and 0. The nickel compound is black with a metallic luster and has a bulk density of approximately 1.34 grams per/mi. The compound catalyzes the decomposition of diethylether.

Ferromagnetism is induced or enhanced by irradiating a sample with either fluorescent light or sunlight with an optimum wavelength between 600 and 400 nm. Ferromagnetism is induced or enhanced by increasing the temperature of a sample to at least about 20° C., preferably 70°–90° C. Higher temperatures provide a stronger response. The ferromagnetic compounds show a non-linear ferromagnetic response with respect to externally applied magnetic fields with the response increasing with increasing fields. Not wishing to be bound by theory, it is believed that when the conduction band reaches a critical electron density, the exchange interaction induces the ferromagnetic transition. This critical electron density can be reached by either photon excitation or by thermal excitation or both. The energy gap of the material is a function of the applied external magnetic field and decreases as field strength increases since the energy of the conduction electrons are lowered. This applied external field can be coupled with the excitation of electrons with photons or thermal energy. The material is either semiconducting or semimetallic.

Not wishing to be bound by theory, it is believed that the structures and stoichiometry of these compounds is indicative of a superconducting transition within these compounds at some temperature. It is also believed the mixed transition metal compounds will provide electrical properties different from those compounds having only one transition metal. For example, a compound with Fe(II) is expected to be semiconducting based on a diagram of its molecular orbitals and a compound with Fe(III) is expected to be conducting. A compound with both Fe(III) and Fe(II) would transfer from semiconductive to a metal-like conductor as the proportion of Fe(III) is increased. Metal-like compounds are expected to have 60–100 mol % Fe(III) and semimetallics are expected to have 0–60 mol % Fe(III).

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents, and publications, cited above and below, are hereby incorporated by reference.

EXAMPLE

Nickel chloride and calcium carbide in a 1:2 molar ratio in a solid state (anhydrous) were heated with a protective argon purge gas at 1 atm in a quartz reactor. The crucible was open to the purge gas. An electric oven was used to provide a temperature of about 970° C. for 24 minutes. During heating, a color change in the starting materials was noticed after two minutes and, following 24 minutes, the color change was complete resulting in a black/white powder. Following heating, the reactants were washed with distilled/deionized water for one hour to remove the soluble salt byproducts and unreacted starting materials such as $CaCl_2$ and $NiCl_2$ and also to remove excess $CaC_2$. The product was then dried for several weeks in a desiccator. The product was anhydrous after heating. The resulting product was plated out to provide a shiny black powder with a density of about $1.8 \pm 0.5$ g/cm$^3$. The compound remained inert for about one year with no oxidation, even when heated to a temperature of about 70° C. When added to diethylether, the solution bubbled, showing indications of a reaction without a loss of material, suggesting catalysis. The combustion temperature was found to be about 200° C.–300° C. which yielded a green and white powder.

An IR spectrum and X-ray diffraction spectrum were taken of the anhydrous product. Diffraction and IR spectra showed the presence of $Ca(OH)_2$, $CaCO_3$ and Ni metal and unusual peaks attributed to one of the inventive compounds in the mixture. The Ni metal may have been formed by decomposition of $NiCl_2$ since it is known that the ionic salt carbides reduce transition metal halides at temperatures of about 700° C.

The IR Spectra

Figure 5:
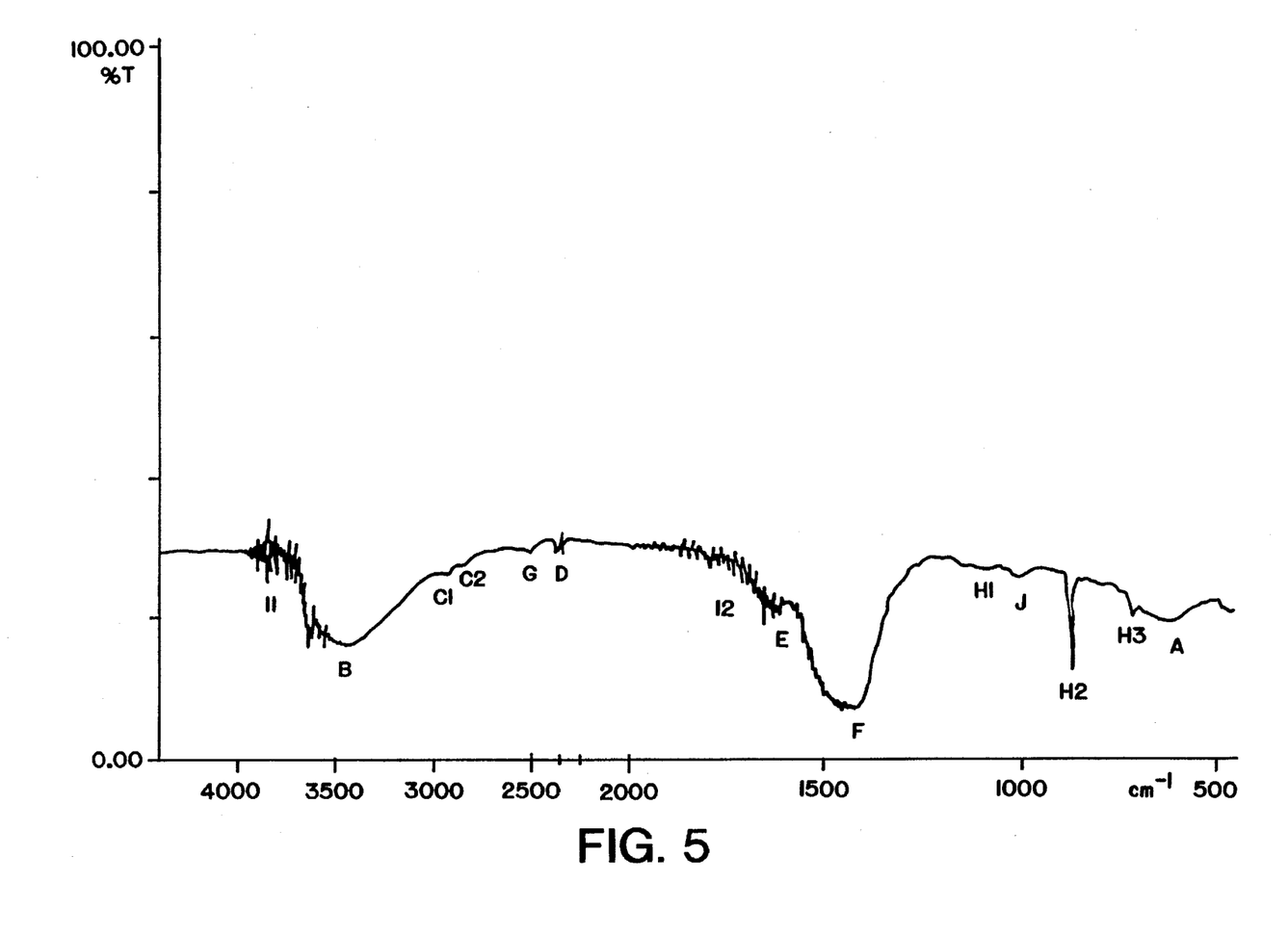
FIG. 5 is an infrared spectrum of a compound of the present invention.

FIG. 5 is the IR spectrum of a compound produced by the method above. The broad band from 3000–3600 cm$^{-1}$ is assigned the OH stretch of $Ca(OH)_2$ and possibly water of hydration. The broad band at 1200–1400 cm$^{-1}$ is assigned to $CaCO_3$ and $Ca(OH)_2$. The two bands at 2924 cm$^{-1}$ and 2875 cm$^{-1}$ correlate with the compound $K_2Pt(C_2CH_3)_2$. However, the bands are due more likely to the analogous species such as $M(X)_{2/x}Ni(C_2R)_4$ on the surface. These compounds are most likely formed by reaction with impure acetylides present in $CaC_2$. The peak at 2349 cm$^{-1}$ is $CO_2$. The peaks at 1087 cm$^{-1}$ (H1), 875 cm$^{-1}$ (H2) and 712 cm$^{-1}$ (H3) are $CaCO_3$. The jagged bands at 3600–4000 cm$^{-1}$ and 1600–2000 cm$^{-1}$ are free water (12). The peaks at 2500 cm$^{-1}$ (G) and 1000 cm$^{-1}$ (J) have not been assigned at this time. The broad peak at 1625 cm$^{-1}$ (E) is assigned to water of hydration. The presence of water of hydration in the spectrum may indicate the unknown material is hygroscopic, since $Ca(OH)_2$ and $CaCO_3$ do not form hydrates. The band at 625 cm$^{-1}$ is believed to be Ni-C stretching. The approximate location of a nickel acetylenic carbon stretch in free molecules is 585 cm$^{-1}$, and, therefore, this black powder product does not comprise free molecules.

X-ray Diffraction

An X-ray powder diffraction pattern was recorded and an elemental analysis was also done. Confining the powder diffraction file search with the elemental analysis allowed for identification of Ni metal, calcium hydroxide and $CaCO_3$. The intense lines remaining define a compound of the present invention. This showed a low intensity line of 7.98 Å. The elemental analysis showed the presence of Ca, Ni and lesser amounts of Cl and Mg, some Si, Al and S. The spectrum was recorded on an electron microscope equipped for elemental analysis. However, this procedure did not allow for identification of carbon.

Figure 4:
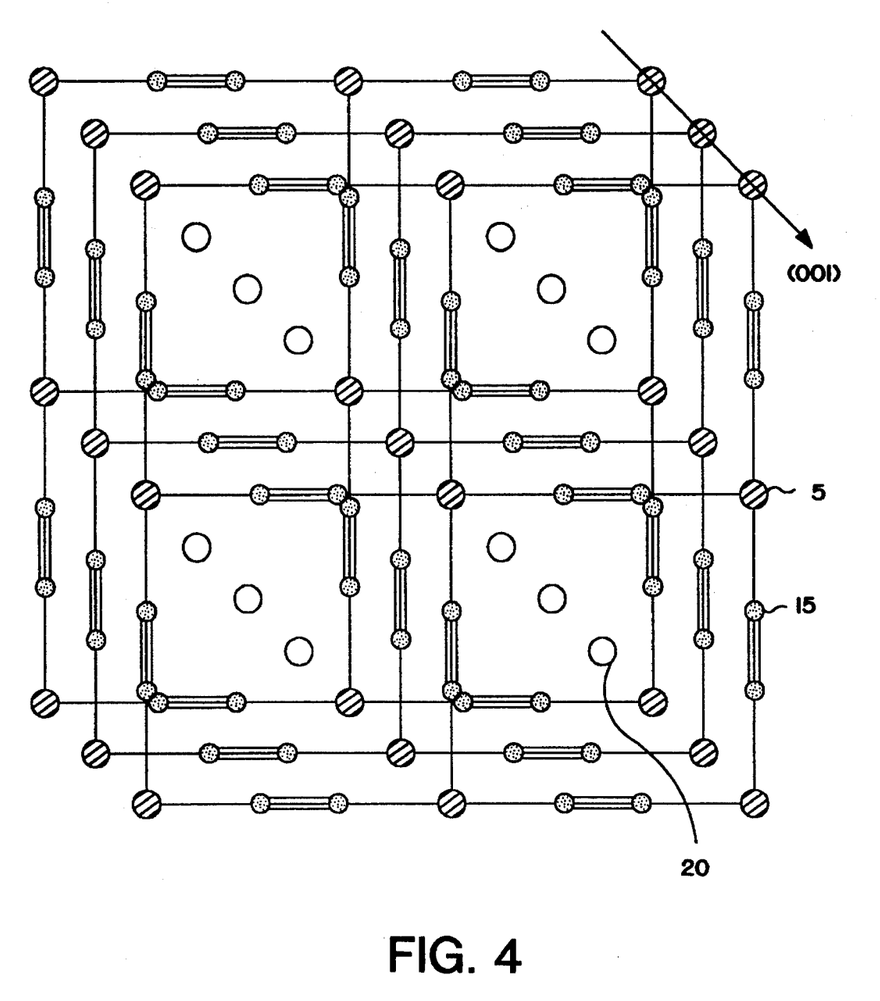
FIG. 4 is a representation of the atomic structure of a planar compound of the present invention with cations shown.

FIG. 4 shows a representation of the structure of a tetracarbide, the transition metals 5, acetylene carbons 15 and cations 20 are shown but the water molecules are not shown. A tetragonal unit cell with a=b=10.13 Å, c=13.25 Å is indexed from the X-ray diffraction powder pattern taken of the compound formed. The dimensions of the a and b axes are consistent with the experimental data on the bond lengths and bond angles of nickel acetylides.

The compound was found to be ferromagnetic with the ferromagnetic properties being induced or enhanced upon exposure to fluorescent light or sunlight. The ferromagnetism was demonstrated visually. The compound was also found to have ferromagnetic properties which persist after irradiation as long as 1–3 hours, showing a gradual decay.

The compound is also thermomagnetic. Heating the compound to about 70°–80° C. induced or enhanced magnetic properties. Thermomagnetism is found at temperatures of 20° C. and higher.

Exposing the compound to a magnetic field also enhanced ferromagnetic behavior in response to light and heat. Exposure to high magnetic strengths allowed incandescent light to induce ferromagnetism. Ferromagnetism induced under these conditions is shown with the same test magnets used to show ferromagnetism under fluorescent light. Not wishing to be bound by theory, high magnetic field strengths are expected to reduce the band gap, allowing such frequencies to provide the desired response.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A solid compound comprising a transition metal selected from the group consisting of Ni(II), Pd(II), Pt(II), Au(III), Ir(I), Rh(I) which is covalently bonded to carbon and which is free of hydrogen covalently bonded to carbon, wherein the infrared spectra of said compound has a fingerprint peak within the range of 595 $cm^{-1}$ to 655 $cm^{-1}$.

2. A solid compound comprising a transition metal selected from the group consisting of Fe(II), Fe(III), Co(II), Co(III), Cr(III), Mn(II), Mn(III), Mo(II), Os(II), Rh(III), Ru(III) and Ir(III) which is covalently bonded to carbon and which is free of hydrogen covalently bonded to carbon, wherein the infrared spectra of said compound has a fingerprint peak within the range of 595 $cm^{-1}$ to 655 $cm^{-1}$.

3. A solid compound comprising nickel which is covalently bonded to carbon and which is free of hydrogen covalently bonded to carbon, wherein the infrared spectra of said compound has a peak at about 625 $cm^{-1}$ when hydrated, and the X-ray powder diffraction spectra of said compound has a peak at about 7.98 Å when hydrated.

4. A solid compound containing at least one acetylide ligand with a planar structure comprising a transition metal selected from the group consisting of Ni(II), Pd(II), Pt(II), Au(III), Ir(I), and Rh(I) which is covalently bonded to carbon and which is free of hydrogen covalently bonded to carbon, having a density of less than 5 $gm/cm^3$.

5. A solid compound with a 3-dimensional structure comprising a transition metal selected from the group consisting of Fe(II), Fe(III), Co(II), Co(III), Cr(III), Mn(II), Mn(III), Mo(II), Os(II), Rh(III), Ru(III) and Ir(III) which is covalently bonded to carbon and which is free of hydrogen covalently bonded to carbon having a density of less than 3 $gm/cm^3$.

6. A solid planar compound comprising a transition metal selected from the group consisting of Ni(II), Pd(II), Pt(II), Au(III), Ir(I), and Rh(I) and acetylide ligands having a unit cell with two axes, a and b, independently having dimensions of a value of from 4.9N Å to 5.1N Å, wherein N is a multiplier less than 100.

7. A solid compound with a 3-dimensional structure comprising a transition metal selected from the group consisting of Fe(II), Fe(III), Co(II), CO(III), Cr(III), Mn(III), Mn(III), Mo(II), Os(II), Rh(III), RU(III) and Ir(III) and acetylide ligands having a unit cell with the axes a, b, c independently having dimensions of a value of from 4.9N Å to 5.1N Å, wherein N is a multiplier less than 100.

8. A solid compound comprised of nickel and acetylide ligands having a planar structure and a unit cell with two axes, a and b, having a dimension of about 10.13 Å.

9. A compound with repeating units of the formula $M(X)_{(4-Y)/x}M_C(Y)C_4$ wherein $M_C(Y)$ is a transition metal selected from the group consisting of Ni(II), Pd(II), Pt(II), Au(III), Ir(I), Rh(I), with Y being its ionic state. M(X) is a counter cation selected from the group consisting of alkali metals, alkaline earth metals and rare earth metals with X being its ionic state and $C_4$ includes acetylide ligands.

10. A compound with repeating units of the formula $M(X)_{(6-Y)/x}M_C(Y)C_6$ wherein $M_C(Y)$ is a transition metal selected from the group consisting of Fe(II), Fe(III), Co(II), Co(III), Cr(III), Mn(II), Mn(III), Mo(II), Os(II), Rh(III), Ru(III) and Ir(III) with Y being its ionic state, M(X) is a counter cation selected from the group consisting of alkali metals, alkaline earth metals and rare earth metals with X being its ionic state and $C_6$ includes acetylides ligands.

11. A solid compound with repeating units of the formula selected from the group consisting of $M(X)_{2/x}NiC_4$, $M(X)_{3/x}FeC_6$, $M(X)_{3/x}CoC_6$, $M(X)_{4/x}CoC_6$ and $M(X)_{4/x}FeC_6$, wherein M(X) is a cation selected from the group consisting of alkali metals alkaline earth metals and rare earth metals with being its ionic state, and $C_4$ and $C_6$ include acetylide ligands.

12. A solid compound comprising a transition metal selected from the group consisting of Ni(II), Pd(II), Pt(II), Au(III), Ir(I), Rh(I), Fe(II), Fe(III), Co(II), Co(III), Cr(III), Mn(II), Mn(III), Mo(II), Os(II), Rh(III), Ru(III) and Ir(III) obtained by reacting an anhydrous transition metal halide with alkali metal acetylide ($C_2^{2-}$) or alkaline earth metal acetylide ($C_2^{2-}$) in an inert atmosphere at a temperature above 300° C. for 3 minutes or more.

13. A compound as in claim 12, wherein the reactants are heated for at least 24 minutes at 970° C. under a protective blanket of silicon carbide or purge gas of argon at 1 ATM.

14. A compound as in claim 12, wherein the transition metal is nickel.

15. A method for preparing a solid transition metal compound having a planar structure comprising reacting in a solvent a transition metal tetraacetylide complex of the formula $M(X)_{(4-Y)/x}M_C(Y)(C_2H)_4$ and a transition metal salt of the formula $M(X)_{(4-Y)/x}M_C(Y)Z_4$ in the presence of a catalyst selected from copper (I) salts of the formula Cu(I)Z, $AgClO_2$, AlBN and $Bu_3B/O_2$, wherein $M_C(Y)$ is a transition metal selected from the group consisting of Ni(II), Pd(II), Pt(II), Au(III), Ir(I), and Rh(I), with Y being its ionic state and M(X) is a cation selected from the group consisting of alkali metals, alkaline earth metals, rare earth metals and ammonium ions ($NH_4^+$), with X being its ionic state and Z is a halide or carboxylate.

16. A method for preparing a solid transition metal compound having a 3-dimensional structure comprising reacting in a solvent a transition metal hexaacetylide complex of the formula $M(X)_{(6-Y)/x}M_C(Y)(C_2H)_6$ and a transition metal salt of the formula $M(X)_{(6-Y)/x}M_C(Y)Z_6$ in the presence of a catalyst selected from copper (I) salts of the formula Cu(I)Z, $AgClO_3$, AlBN and $Bu_3B/O_2$, wherein $M_C(Y)$ is a transition metal selected from the group consisting of Fe(II), Fe(III), Co(II), Co(III), Cr(III), Mn(II), Mn(III), Mo(II), Os(II), Rh(III), Ru(III) and Ir(III), with Y being its ionic state and M(X) is a cation selected from the group consisting of alkali metals, alkaline earth metals and rare earth metals, X being its ionic state and Z is a halide or carboxylate.

17. A method as in claim 15, wherein the transition metal is nickel.

18. A method as in claim 15, wherein the transition metal tetraacetylide complex is obtained by reacting a transition metal salt of the formula $M(X)_{(4-Y)/x}M_C(Y)Z_4$ with acetylene in the presence of a catalyst.

19. A method as in claim 16, wherein the transition metal hexaacetylide complex is obtained by reacting a transition metal salt of the formula $M(X)_{(6-Y)/x}M(Y)Z_6$ with acetylene in the presence of a catalyst.

20. A method as in claim 15, wherein the transition metal tetraacetylide is obtained by reacting a transition metal thiocyanate or cyanide and alkali earth metal salt of acetylide in solvent.

21. A method as in claim 16, wherein the transition metal hexaacetylide is obtained by reacting a transition metal thiocyanate or cyanide and alkali earth metal salt of acetylide in solvent.

22. A ferromagnetic solid compound comprising nickel which is covalently bonded to carbon and which is free of hydrogen covalently bonded to carbon having a density of less than 5 gm/cm$^3$.

23. A ferromagnetic solid compound comprising iron or cobalt which is covalently bonded to carbon and which is free of hydrogen covalently bonded to carbon having a density of less than 3 gm/cm$^3$.

24. A ferromagnetic composition comprising nickel, iron or cobalt which is covalently bonded to carbon and which is free of hydrogen covalently bonded to carbon having ferromagnetic properties induced or enhanced by exposure to photo energy, thermal energy or both.

25. A ferromagnetic solid compound as in claim 22, comprising nickel which is covalently bonded to carbon and which is free of hydrogen covalently bonded carbon having ferromagnetic properties induced or enhanced by exposure to electromagnetic radiation having a wavelength in the range of 400–600 nm at ambient temperature when hydrated or dehydrated.

26. A ferromagnetic solid compound as in claim 22, having ferromagnetic properties which are temperature dependent.

27. A ferromagnetic solid compound as in claim 22, having ferromagnetic properties which are induced or enhanced with increasing temperature.

28. A ferromagnetic compound as in claim 22, wherein the frequency of electromagnetic radiation to which the ferromagnetic properties respond and the intensity of the response varies upon application of an external magnetic field to said compound.

29. A solid compound comprising more than one transition metal selected from the group consisting of Ni(II), Pd(II), Pt(II), Au(III), Ir(I), Rh(I) which is covalently bonded to carbon and which is free of hydrogen covalently bonded to carbon, wherein the infrared spectra of said compound has a fingerprint peak within the range of 595 cm$^{-1}$ to 655 cm$^{-1}$ having a density of less than 5 gm/cm$^3$.

30. A solid compound comprising more than one transition metal selected from the group consisting of Fe(II), Fe(III), Co(II), Co(III), Cr(III), Mn(II), Mn(III), Mo(II), Os(II), Rh(III), Ru(III) and Ir(III) which is covalently bonded to carbon and which is free of hydrogen covalently bonded to carbon, wherein the infrared spectra of said compound has a fingerprint peak within the range of 595 cm$^{-1}$ to 655 cm$^{-1}$ having a density of less than 3 gm/cm$^3$.

31. A compound comprising two or more transition metals selected from the group consisting of Ni(II), Pd(II), Pt(II), Au(III), Ir(I), Rh(I), each within different repeating units of the formula $M(X)_{(4-Y)/x}M_C(Y)C_4$ wherein $M_C(Y)$ is a transition metal with Y being its ionic state and M(X) is a counter cation selected from the group consisting of alkali metals, alkaline earth metals and rare earth metals with X being its ionic state, wherein $C_4$ includes acetylide ligands.

32. A compound comprising two or more transition metals selected from the group consisting of Fe(II), Fe(III), Co(II), Co(III), Cr(III), Mn(II), Mn(III), Mo(II), Os(II), Rh(III), Ru(III), each within different repeating units of the formula $M(X)_{(6-Y)/x}M_C(Y)C_6$ wherein $M_C(Y)$ is transition metal with Y being its ionic state and M(X) is a counter cation selected from the group consisting of alkali metals, alkaline earth metals and rare earth metals with X being its ionic state, wherein $C_6$ includes acetylide ligands.

33. A compound comprising more than one transition metal selected from either the group consisting of Ni(II), Pd(II), Pt(II), Au(III), Ir(I), Rh(I) or the group consisting of Fe(II), Fe(III), Co(II), Co(III), Cr(III), Mn(II), Mn(III), Mo(II), Os(II), Rh(III), Ru(III) and Ir(III) obtained by reacting more than one anhydrous transition metal halide with alkali metal, acetylide ($C_2^{2-}$) or alkaline earth metal acetylide ($C_2^{2-}$) in an inert atmosphere at a temperature above 300° C. for 3 minutes or more.

34. A method for preparing a solid transition metal compound with mixed transition metals having a planar structure comprising reacting in a solvent a transition metal tetraacetylide complex of the formula $M(X)_{(4-Y)/x}M_C(Y)(C_2H)_4$ with a transition metal salt of the formula $M(X)_{(4-Y)/x}M_C(Y)Z_4$ in the presence of a catalyst selected from copper (I) salts of the formula Cu(I)Z, AgClO$_2$, AIBN and Bu$_3$B/O$_2$, wherein two or more transition metal salts and/or two or more transition metal complexes are utilized, $M_C(Y)$ is a transition metal selected from the group consisting of Ni(II), Pd(II), Pt(II), Au(III), Ir(I), and Rh(I), with Y being its ionic state; M(X) is a cation selected from the group consisting of alkali metals, alkaline earth metals, rare earth metals and ammonium ions (NH$_4^+$), with X being its ionic state and Z is a halide or carboxylate.

35. A method for preparing a solid transition metal compound with mixed transition metals having a 3-dimensional structure comprising reacting in a solvent a transition metal hexaacetylide complex of the formula $M(X)_{(6-Y)/x}M_C(Y)(C_2H)_6$ with a transition metal salt of the formula $M(X)_{(6-Y)/x}M_C(Y)Z_6$ in the presence of a catalyst selected from copper (I) salts of the formula Cu(I)Z, AgClO$_3$, AIBN and Bu$_3$B/O$_2$, wherein two or more transition metal salts and/or two or more transition metal complexes are utilized, $M_C(Y)$ is a transition metal selected from the group consisting of Fe(II), Fe(III), Co(II), Co(III), Cr(III), Mn(II), Mn(III), Mo(II), Os(II), Rh(III), Ru(III) and Ir(III), with Y being its ionic state and M(X) is a cation selected from the group consisting of alkali metal, alkaline earth metals and rare earth metals, X being its ionic state and Z is a halide or carboxylate.

36. A compound with repeating units of the formula $M(X)_{(4-Y)/x}M_C(Y)C_{4n}$ wherein n=1–6, and $M_C(Y)$ is a transition metal selected from the group consisting of Ni(II), Pd(II), Pt(II), Au(III), Ir(I), Rh(I), with Y being its ionic state and M(X) is a counter cation selected from the group consisting alkali metals, alkaline earth metals and rare earth metals with X being its ionic state, wherein $C_{4n}$ includes acetylide ligands where n=1.

37. A compound with repeating units of the formula $M(X)_{(6-Y)/x}M_C(Y)C_{6n}$ wherein n=1–6, and $M_C(Y)$ is a transition metal selected from the group consisting of Fe(II), Fe(III), Co(II), Co(III), Cr(III), Mn(II), MN(III), Mo(II), Os(II), Rh(III), Ru(III) and Ir(III) with Y being its ionic state and M(X) is a counter cation selected from the group consisting of alkali metals, alkaline earth metals and rare earth metals with X being its ionic state, wherein $C_{6n}$ includes acetylide ligands where n=1.

38. A method for preparing a solid compound comprising a transition metal selected from the group consisting of Ni(II), Pd(II), Pt(II), Au(III), Ir(I), Rh(I), Fe(II), Fe(III), Co(II), Cr(III), Mn(II), Mn(III), Mo(II), Os(II), Rh(III), Ru(III) and Ir(III) which comprises reacting an anhydrous transition metal halide with an alkali metal acetylide ($C_2^{2-}$) or alkaline earth metal acetylide ($C_2^{2-}$) in an inert atmosphere at a temperature above 300° C. for 3 minutes or more.

39. A method as in claim 38, wherein the reactants are heated for at least 24 minutes at 970° C. under a protective blanket of silicon carbide or purge gas of argon at 1 ATM.

40. A method as in claim 38, wherein the transition metal is nickel.

41. A method for preparing a solid compound comprising two or more transition metals selected from the group consisting of Ni(II), Pd(II), Pt(II), Au(III), Ir(I), Rh(I), Fe(II), Fe(III), Co(II), Cr(III), Mn(II), Mn(III), Mo(II), Os(II), Rh(III), Ru(III) and Ir(III) which comprises reacting two or more anhydrous transition metal halides with an alkali metal acetylide ($C_2^{2-}$) or alkaline earth metal acetylide ($C_2^{2-}$) in an inert atmosphere at a temperature above 300° C. for 3 minutes or more.

42. A metal as in claim 41, wherein the reactants are heated for at least 24 minutes at 970° C. under a protective blanket of silicon carbide or purge gas of argon at 1 ATM.

\* \* \* \* \*